(12) United States Patent
Orlowski et al.

(10) Patent No.: US 6,365,134 B1
(45) Date of Patent: Apr. 2, 2002

(54) PROCESS AND COMPOSITION FOR HIGH EFFICACY TEETH WHITENING

(75) Inventors: Jan A. Orlowski, Altadena; David V. Butler, West Covina, both of CA (US)

(73) Assignee: Scientific Pharmaceuticals, Inc., Pomona, CA (US)

( * ) Notice: Subject to any disclaimer, the term of this patent is extended or adjusted under 35 U.S.C. 154(b) by 0 days.

(21) Appl. No.: 09/618,567

(22) Filed: Jul. 17, 2000

Related U.S. Application Data

(63) Continuation of application No. 09/348,456, filed on Jul. 7, 1999, now abandoned.

(51) Int. Cl.⁷ .............................. A61K 7/16; A61K 7/20; A61K 33/40
(52) U.S. Cl. ............................ 424/53; 424/49; 424/613
(58) Field of Search ...................................... 424/49–58

(56) References Cited

U.S. PATENT DOCUMENTS

| | | | |
|---|---|---|---|
| 3,499,844 A | | 3/1970 | Kibbel, Jr. et al. |
| 3,657,413 A | | 4/1972 | Rosenthal et al. |
| 4,990,089 A | | 2/1991 | Munro |
| 5,076,791 A | | 12/1991 | Madray, Jr. |
| 5,098,303 A | | 3/1992 | Fischer |
| RE34,196 E | | 3/1993 | Munro |
| 5,234,342 A | | 8/1993 | Fischer |
| 5,376,006 A | | 12/1994 | Fischer |
| 5,409,631 A | | 4/1995 | Fischer |
| 5,425,953 A | | 6/1995 | Sintov et al. |
| 5,597,554 A | * | 1/1997 | Wagner ........................ 424/53 |
| 5,631,000 A | | 5/1997 | Pellico et al. |
| 5,643,428 A | | 7/1997 | Yarborough |
| 5,645,428 A | * | 7/1997 | Yarborough ................. 433/215 |
| 5,713,738 A | * | 2/1998 | Yarborough ................. 433/215 |
| 5,718,886 A | | 2/1998 | Pellico |
| 5,851,514 A | * | 12/1998 | Hassan et al. ................. 424/53 |
| 5,902,568 A | * | 5/1999 | Ryles et al. .................... 424/53 |

FOREIGN PATENT DOCUMENTS

| | | | |
|---|---|---|---|
| GB | 2 117240 | * | 10/1983 |
| WO | 97/02805 | * | 1/1997 |
| WO | 97/0777 | * | 3/1997 |
| WO | 97/07777 | | 3/1997 |
| WO | 97/11676 | * | 4/1997 |
| WO | 98/23219 | * | 6/1998 |
| WO | 98/31331 | * | 7/1998 |
| WO | 99/20226 | * | 4/1999 |

OTHER PUBLICATIONS

Council on Scientific Affairs, ADA, "Home–Use Tooth Whitening Products", Jan. 1998/DRAFT, pp. 1–15.

* cited by examiner

*Primary Examiner*—Shep K. Rose
(74) *Attorney, Agent, or Firm*—Knobbe, Martens, Olson & Bear LLP

(57) ABSTRACT

A process and composition for bleaching teeth made up of two formulations blended together before each application. The invention offers faster results while significantly reducing the possibility of user discomfort. One of said formulations contains hydrogen peroxide (in a free form or in the form of an adduct), the other contains salts and hydroxides and/or oxides of metals belonging to the first or second group of the Periodic Table which stimulate the generation of radical oxygen. The invention allows for balancing pH and assuring adequate water concentration to avoid tissue desiccation and user discomfort without compromising shelf life of the device.

16 Claims, No Drawings

PROCESS AND COMPOSITION FOR HIGH EFFICACY TEETH WHITENING

This application is a continuation of Ser. No. 09/348456 filed Jul. 7, 1999 abandoned.

BACKGROUND OF THE INVENTION

Teeth whiteners, also known as teeth bleaching agents, are in widespread use as a cosmetic means to enhance appearance and, generally, to contribute to better oral health and hygiene.

Particularly popular and most effective among these devices are those whose chemistry is based on peroxides, of which hydrogen peroxide and carbamide peroxide (representing an adduct of hydrogen peroxide and urea) are most frequently employed. Such peroxides are characterized by their lack of stability resulting in the generation of radical (atomic) oxygen, the chemical action of which is responsible for the desired whitening/bleaching effect. The generation of atomic oxygen is, however, highly undesirable during storage of such peroxide-based teeth whitening devices. Thus, in their commercial form, such devices are formulated in a manner designed to prevent and/or inhibit premature peroxide decomposition. Contact with certain foreign objects, especially materials having highly developed surface areas; certain chemicals; and elevated pH accelerate the decomposition process of said peroxides and the liberation of radical oxygen.

Stability of such formulations, however, is in direct conflict with the purpose and objective of their applications, namely achieving the best possible whitening effect in the shortest possible time of contact with the tooth surface. Consequently, teeth whitening devices of prior art formulations typically require multiple applications stretching over a period of weeks and even months, with each recommended application time usually being from two to eight hours.

Of the two forms of peroxides commonly used in commercial teeth whiteners, hydrogen peroxide is preferred for its faster action, while carbamide peroxide based formulations offer advantages in terms of greater storage stability, more desirable consistencies and handling properties, and less risk of damage to soft tissues. Stability of both hydrogen peroxide and carbamide peroxide-based formulations is greater, especially in the case of the former, at low pH, preferably in the range of 3–4.5. Carbamide peroxide based materials may, however, exhibit adequate stability even at neutral or near neutral pH. This makes such formulations more desirable from the standpoint of better perceived compatibility with mucosa and of having no or negligible detrimental effect on tooth enamel and on the health of teeth that are in less than intact condition.

Carbamide peroxide formulations are particularly stable in environments containing little or no water. Examples of carriers for carbamide peroxide most common to commercial use are glycerin and propylene glycol. While these carriers are considered nontoxic and convenient for their compatibility with desirable additives such as thickening agents, preservatives, flavors and therapeutics, their use may create some unwelcome, though generally minor, side effects. The most common side effect is discomfort caused by the desiccating effect of anhydrous (or nearly anhydrous) hydrophilic solvents/carriers on mucosa, especially pronounced when scarified or inflamed tissue is involved. Similar responsed may also be expected in cases of leaching restorations or recessed gums.

The concentrations of peroxides in commercially available teeth bleaching formulations varies greatly, generally depending on factors such as recommended time of a single application; frequency and technique of application; and most of all, the intended use: if the material is designed for professional use only, for application by the user/patient but under professional control, or broadly available to the public for in-home, non-supervised use.

The concentration of peroxide (expressed as a percentage of $H_2O_2$) in carbamide peroxide or hydrogen peroxide based formulations sold directly to the public is generally on the order of 3.4%, which corresponds to a 10% concentration of carbamide peroxide. The concentration of $H_2O_2$ in formulations designed for professional use is often higher, in the 5–10% range.

To provide prolonged contact of whitening formulation with teeth, while minimizing the contact with mucosa, the whitening material is usually placed on fabricated trays, preferably ones custom procured in a dentist's office to precisely fit the patient's anatomy. The use of higher $H_2O_2$ concentration (faster-action) formulations calls for special measures to protect the mucosa from contact with such inherently more irritating compositions. Rubber dams or curable tissue coatings may be used for such purposes.

Attempts have been made to accelerate the teeth bleaching processes without increasing the concentration of the peroxide by using heat-generating devices, such as high intensity light emitting instruments or lasers. Because of the cost of necessary equipment and greatly increased risk of tissue damage associated with these techniques, they are designed for use exclusively by a dentist. Such treatments are necessarily expensive. The most effective of these techniques are those using lasers, but they also carry the highest possibility of inflicting damage on the teeth and/or soft tissue. The cost of treatments is considerably higher than when conventional methods are used.

The shortcomings of the prior art formulations may be summarized as follows:

a) the inherent conflict between the requirements of shelf life stability of peroxides and the understandable demand for fast bleaching action and high efficacy of the product;

b) the more stable (and generally considered safer and more convenient) carbamide peroxide based teeth whiteners require, for adequate storage stability, anhydrous or near anhydrous hydrophillic carriers, frequently causing user discomfort due to their desiccating effect on mucosa;

c) storage stability requirements impose the necessity of maintaining low pH of commercial teeth whitening formulations, especially those based on hydrogen peroxide, this is objectionable from the point of view of the potentially damaging effect of such acidic materials on teeth and mucosa;

d) formulations which exhibit adequate shelf life, evidenced by maintaining stable peroxide concentrations over time, are intrinsically less effective due to the slow generation of radical (atomic) oxygen in the oral environment, which impairs the speed and efficacy of the teeth bleaching process; and e) fast acting techniques require the use of expensive, often unreliable equipment; also they are associated with increased risk to the patients and high cost per treatment; they are not designed, or indicated, for in-home use, but rather for application by dental professionals only.

It is an object of the present invention to provide a fast acting teeth whitening process and composition.

It is a further object of the present invention to provide a teeth whitening composition that has a balanced pH and avoids tissue dessication.

It is also an object of the present invention to provide a formulation that is not compromised by shelf life.

SUMMARY OF THE INVENTION

The invention includes a new teeth whitening system including two components separated from one another during storage. The components are mixed shortly, or immediately, before their application to the teeth. The whitening system includes two parts, the first part containing 2–10% by weight hydrogen peroxide in a free form or in the form of an adduct with urea (carbamide peroxide) dissolved or suspended in a solvent/carrier. The second part of the teeth whitening system is of a gel or paste consistency employing water as the sole or one of the carriers/mediums of suspended and/or dissolved salts, oxides or hydroxides of metals belonging to the first or second group of the Periodic Table.

DETAILED DESCRIPTION OF THE INVENTION

The invention relates to a new teeth whitening or bleaching system having two component parts. The component parts are separated from each other during storage, but are mixed shortly or immediately before their application. While conventionally used peroxides may be employed as active ingredients of the formulations of this invention, their potential for damaging teeth and oral soft tissues has been virtually eliminated, while, unexpectedly, the speed of the teeth whitening process has been dramatically increased. This allows for a shortening of the application time. Thus results comparable to prior formulations are achieved in a fraction of the time required by such prior formulations.

Some important additional advantages may be realized from the herein disclosed invention, including greatly reduced user discomfort caused by the desiccation or irritation of soft oral tissues. Also, the invention eliminates the deleterious effects of prior teeth whiteners on tooth enamel caused by their low pH and the often unavoidable presence of acids.

No special instruments are necessary or indicated in relation with the teeth whitening process of this invention.

The teeth whitening compositions of this invention are composed of two integral parts. The first part contains 2–10% by weight hydrogen peroxide in a free form or in the form of an adduct with urea (carbamide peroxide), dissolved or suspended in a suitable solvent/carrier such as water, glycerin, or propylene glycol.

Suitable thickeners may be added to such a mixture to achieve a desirable consistency to facilitate application and to slow the dissolution process in order to prolong the bleaching or whitening action.

Anhydrous carriers such as glycerin, ethyl alcohol, propylene glycol and polyalkylene glycols are preferable for formulations based on carbamide peroxide for achieving the greatest stability and tolerance to storage conditions. Water is the primary solvent for formulations based on hydrogen peroxide.

The second component of the teeth bleaching or whitening system of this invention is of a gel or paste consistency. Water is the principal, or one of the carrier(s) serving as a medium in which are dissolved or suspended salts, oxides, and/or hydroxides of metals belonging to the first or second group of the Periodic Table including sodium, potassium, magnesium and/or calcium. Among such salts, those containing anions derived from weak acids such as acetic, acrylic, glutaric, methacrylic, etc. are preferred.

Oxides or hydroxides of sodium, potassium, calcium and magnesium were found to be particularly suitable as components of the formulations of this invention. Incorporation of fluoride salts such as stannous fluoride, sodium monofluorophosphate or sodium fluoride may add additional benefits to the teeth treatments of this invention.

Common thickening and suspending agents may be used to optimize the consistency of the system components. Preferred thickening agents are alkaline salts of polyacrylic acid, amine crosslinked polyacrylic acid, polyethylene oxide, cellulose derivatives, water soluble natural gums, gelatin and starch.

Flavoring and coloring agents may be added to enhance the acceptance or appeal of the material, or as indicators of the progress of radical oxygen generation and the reactivity of peroxide. The most desirable flavors may include, among others, food grade orange, lemon, peppermint, spearmint, mint, bubble gum, cherry, watermelon, strawberry and apple varieties. As coloring agents FD&C or D&C water soluble dyes may be used; FD&C Blue #1 and FD&C Blue #2 are preferred. The coloring and/or flavoring agents are preferably, but not necessarily, incorporated in the second part of the system, i.e. the part not containing peroxides.

The pH of the components of the system of this invention are important. The part containing peroxide (Part One) can be adjusted by means of using buffering additives to maintain a pH value of 3–7.5, preferably 3.5–5.5. The part not containing peroxide should have a pH above 8, preferably in the range of 9–12. Mixture of the parts, at proportions as indicated for use, should show pH values of 8–12, preferably 8.5–10.5.

It was found that teeth bleaching systems according to this invention are more effective than those in the past when difficult to whiten teeth are involved. The systems are faster in their bleaching action, thus allowing for shorter application times or less frequent applications while delivering superior results. It was also unexpectedly found that such teeth bleaching systems are very well tolerated by the soft oral tissue and are unlikely to irritate mucosa or cause discomfort. Astonishingly good appearance and good health of teeth after bleaching were attributed to the presence of mineralizing agents, especially calcium salts.

It was also unexpected to find that oral tissue can tolerate elevated pH of 8.5–11.5 for the short periods of time sufficient to achieve easily noticeable teeth whitening effects. Obtaining comparable results using conventional teeth whitening materials would require application times up to 100 times longer.

Examples and Properties of the Teeth Whitening Formulations of this Invention (All Percentages are Weight Percents)

The preferred embodiment of this invention is illustrated in Examples 1–5 below.

EXAMPLE 1

The teeth bleaching system consisted of:

Part 1:

| | |
|---|---|
| carbamide peroxide | 22% |
| glycerin | 76.8% |
| partially neutralized polycarboxylic acid | 2.2% |

Part 2:

| | | | |
|---|---|---|---|
| water | 63% | FD&C Blue #1 | 0.2% |
| calcium carbonate | 9% | silica | 4% |
| sodium carbonate | 1.8% | carboxymethyl cellulose | 3% |
| sodium bicarbonate | 3% | glycerin | 16% |

The parts were mixed together at a volumetrically 1:1 ratio. The pH of the mixture was 10.8.

Laboratory Testing

The rate of generation of free oxygen was tested by redox colorimetric method at body temperatures of 37° C. It was found that the generation of radical oxygen was an order of magnitude faster in the two component system than in a system comprising Part 1 only. The blue color indicator in Part 2 remained unchanged even after six weeks of exposure at 37° C. When the indicator was added to Part 1 instead of Part 2, the color still remained pronounced after 72 hours exposure at 37° C. However, after mixing Part 1 and Part 2 together, the color disappeared after one hour.

Clinical studies have confirmed the fast action and high efficacy of this material with no adverse reaction reported and excellent patient acceptance. In a particular clinical case the shade of the treated teeth have changed in a single session from Vita C4 to C1 within 20 minutes after application.

EXAMPLE 2

The bleaching system consisted of:

Part 1:

| | |
|---|---|
| carbamide peroxide | 16% |
| glycerin | 76.7% |
| partially neutralized polyacrylic acid | 2.3% |
| water | 5% |

Part 2:

| | | | |
|---|---|---|---|
| water | 64% | sodium carbonate | 0.5% |
| glycerin | 16% | sodium fluoride | 0.5% |
| carboxymethyl cellulose | 3.8% | FD&C Blue #1 | 0.2% |
| calcium carbonate | 8.5% | silica | 5% |
| sodium bicarbonate | 1.5% | | |

The parts were mixed together at a volumetrically 1:1 ratio.

Laboratory Testing

When Part 1 and Part 2 were mixed together, the color disappeared within 5 hours. Clinical experience with this material is similar to that described in Example 1.

EXAMPLE 3

Part 1:

| | |
|---|---|
| carbamide peroxide | 22% |
| glycerin | 76.8% |
| partially neutralized polycarboxylic acid | 2.2% |

Part 2:

| | | | |
|---|---|---|---|
| water | 67% | carboxymethyl cellulose | 3% |
| glycerin | 15% | xanthum gum | 0.3% |
| calcium carbonate | 7% | silica | 5.7% |
| potassium bicarbonate | 2% | | |

Laboratory Testing

The overall performance of this formulation was substantially similar to that of Example 2.

Other formulations found effective are cited below.

EXAMPLE 4

Part 1:

| | |
|---|---|
| hydrogen peroxide solution | 96% |
| hydroxymethyl cellulose | 2.9% |
| xanthum gum | 1% |
| sodium pyrophosphate | 0.1% |

Part 2:

| | | | |
|---|---|---|---|
| water | 68.8% | sodium bicarbonate | 1% |
| glycerin | 15% | calcium phosphate | 2% |
| calcium carbonate | 3% | hydroxypropyl cellulose | 2% |
| sodium carbonate | 0.2% | polyethylene oxide | 8% |

EXAMPLE 5

Part 1:

| | |
|---|---|
| hydrogen peroxide solution | 86% |
| glycerin | 10% |
| partially neutralized polyacrylic acid | 1% |

Part 2:

| | | | |
|---|---|---|---|
| water | 63% | FD&C Blue #1 | 0.2% |
| calcium carbonate | 9% | silica | 4% |
| sodium carbonate | 1.8% | carboxymethyl cellulose | 3% |
| sodium bicarbonate | 3% | glycerin | 16% |

What is claimed is:

1. A component for whitening teeth comprising:
   a) a first component in the form of a suspension or solution comprising about 6.8% to 34% carbamide peroxide and a substantially anhydrous carrier, said first component having a pH of about 3.0 to 7.5 and being substantially colorless; and
   b) a second component in the form of an aqueous gel or paste comprising one or more alkali materials selected from the group consisting of calcium oxide, sodium hydroxide, potassium hydroxide, potassium bicarbonate, sodium acetate, sodium carbonate, sodium bicarbonate, sodium benzoate, sodium acrylate, sodium methacrylate, sodium gluconate, calcium carbonate, magnesium carbonate, calcium phosphates, calcium bicarbonate, calcium gluconate, calcium silicate and combinations thereof; and FD&C Blue #1, FD&C Blue #2, or combinations thereof as a dye indicator which gradually discolors or loses color when reacted with a radical oxygen; said second component having a pH of about 8.0 to 12;

wherein admixing of said first and second components prior to applying the composition to the teeth provides the composition for whitening teeth having a pH of about 8.0 to 12.

2. The composition of claim 1, wherein the substantially anhydrous carrier is selected from the group consisting of glycerin, ethyl alcohol, propylene glycol, polyalkylene glycols, and combinations thereof.

3. The composition of claim 1, wherein the first component, the second component, or both the first and second components further comprise a thickening agent.

4. The composition of claim 3, wherein the thickening agent is selected from the group consisting of polyacrylic acid, polyacrylic acid salts, amine crosslinked polyacrylic acid, natural gums, gelatin, starch, cellulose derivatives, polyalkalene oxides, and combinations thereof.

5. The composition of claim 1, wherein the composition further comprises sodium fluoride, stannous fluoride, or sodium monofluorophosphate.

6. The composition of claim 1, wherein a ratio of mixing of the first component to the second component is 1:1.

7. A composition for whitening teeth comprising:
a first component in the form of a suspension or solution, said first component being substantially colorless and having a pH of about 3.0 to 7.5 and comprising about 6.8% to 34% carbamide peroxide, and
a substantially anhydrous carrier selected from the group consisting of glycerin, ethyl alcohol, propylene glycol, polyalkalene glycols, and combinations thereof, and
a second component in the form of an aqueous gel or paste, said second component having a pH of about 8.0 to 12 and comprising
one or more alkali materials selected from the group consisting of potassium bicarbonate, sodium carbonate, sodium bicarbonate, calcium carbonate, calcium phosphate, and combinations thereof; and FD&C Blue #1, FD&C Blue #2, or combinations thereof as a dye indicator which gradually discolors or loses color when reacted with a radical oxygen;

wherein admixing of said first and second components prior to applying the composition to teeth provides the composition for whitening teeth having a pH of about 8.0 to 12.

8. The composition of claim 7, wherein the substantially anhydrous carrier is selected from the group consisting of glycerin, ethyl alcohol, propylene glycol, polyalkalene glycols, and combinations thereof.

9. The composition of claim 7, wherein the first component, the second component, or both the first and second components further comprise a thickening agent.

10. The composition of claim 9, wherein the thickening agent is selected from the group consisting of polyacrylic acid, polyacrylic acid salts, amine crosslinked polyacrylic acid, natural gums, gelatin, starch, cellulose derivatives, polyalkalene oxides, and combinations thereof.

11. The composition of claim 7, wherein the composition further comprises sodium fluoride, stannous fluoride, or sodium monofluorophosphate.

12. The composition of claim 7, wherein a ratio of mixing of the first component to the second component is 1:1.

13. A process for whitening teeth, comprising:
mixing first and second components to form a tooth whitening composition,
the first component being in the form of a suspension or solution comprising about 6.8% to 34% carbamide peroxide and a substantially anhydrous carrier, said first component having a pH of about 3.0 to 7.5 and being substantially colorless; and
the second component being in the form of an aqueous gel or paste comprising one or more alkali materials selected from the group consisting of oxides, hydroxides, and weak salts of sodium, potassium, calcium, or magnesium, said second component having a pH of about 8.0 to 12 and FD&C Blue #1, FD&C Blue #2, or combinations thereof as a dye indicator which gradually discolors or loses color when reacted with radical oxygen; and
contacting one or more teeth with the tooth whitening composition for about 10–60 minutes or less.

14. The process according to claim 13, wherein contacting one or more teeth with the tooth whitening composition occurs for about 20 minutes.

15. A process according to claim 13, further comprising placing the tooth whitening composition into a flexible tray or form shaped to fit over one or more teeth in a human mouth prior to contacting said teeth with the composition.

16. A process according to claim 13, wherein the process further comprises separating the teeth from the composition after the dye indicator discolors or loses color.

* * * * *